United States Patent [19]
Bombardelli

[11] Patent Number: 5,917,056
[45] Date of Patent: Jun. 29, 1999

[54] 10-DEACETYL-14β-HYDROXYBACCACTINE III DERIVATIVES, A PROCESS FOR THE PREPARATION THEREOF AND FORMULATIONS CONTAINING THEM

[75] Inventor: Ezio Bombardelli, Milan, Italy

[73] Assignee: INDENA S.p.A., Milan, Italy

[21] Appl. No.: 08/875,770

[22] PCT Filed: May 5, 1996

[86] PCT No.: PCT/EP96/01919

§ 371 Date: Aug. 5, 1997

§ 102(e) Date: Aug. 5, 1997

[87] PCT Pub. No.: WO96/36622

PCT Pub. Date: Nov. 21, 1996

[30] Foreign Application Priority Data

May 19, 1995 [IT] Italy .................................. MI95A1022

[51] Int. Cl.⁶ ...................... C07D 327/10; C07D 317/70; A61K 31/38; A61K 31/335

[52] U.S. Cl. .................. 549/31; 549/34; 549/40; 549/41; 549/229; 549/432; 514/439; 514/443; 514/467

[58] Field of Search ...................... 514/439, 443, 514/467; 549/31, 34, 40, 41, 229, 432, 510

[56] References Cited

FOREIGN PATENT DOCUMENTS 0 559 019    9/1993    European Pat. Off. .
WO 9422856  10/1994    WIPO .

OTHER PUBLICATIONS

Chen et al, Tetrahedron Letters, 34 (20), pp. 3205–3206, 1993.

I. Ojima et al., "Structure–Activity Relationships of New Taxoids Derived from 14β–Hydroxy–10–deacetylbaccatin III", *J. Med. Chem.*, vol. 37 (1994) pp. 1408–1410.

I. Ojima et al., "Synthesis and Biological Activity of 14–Hydroxydocetaxel", *Bioorg. Med. Chem. Lett.*, vol. 4, No. 13 (1994) pp. 1571–1576.

J. Kant et al., "Synthesis and Antitumor Properties of Novel 14–β–Hydroxytaxol and Related Analogues", *Bioorg. Med. Chem. Lett.*, vol. 4, No. 13 (1994) pp. 1565–1570.

E. Didier et al., "2–Monosubstituted–1,3–Oxazolidines as Improved Protective Groups of N–Boc–Phenylisoserine in Docetaxel Preparation", *Tetrahedron Lett.*, vol. 35, No. 15 (1994) pp. 2349–2352.

E. Didier et al., "Expeditious Semisynthesis of Docetaxel Using 2–Trichloromethyl–1,3–Oxazolidine as Side–Chain Protection", *Tetrahedron Lett.*, vol. 35, No. 19 (1994) pp. 3063–3064.

*Primary Examiner*—Ba K. Trinh
*Attorney, Agent, or Firm*—Pennie & Edmonds LLP

[57] ABSTRACT

The present invention relates to novel 10-deacetyl-14β-hydroxybaccatine III derivatives. The novel derivatives, having cytotoxic and antitumour activity, are prepared from this synton after functionalization of the hydroxyls at 1-, 14- as thiocarbonate, iminocarbonate and sulfite and possible oxidation of the hydroxyl at $C_{10}$. These derivatives are subjected to a subsequent esterification at position 13- with a variously substituted isoserine chain. The products of the invention can be administered by the injective or oral route, when suitably formulated.

5 Claims, No Drawings

10-DEACETYL-14β-HYDROXYBACCATINE III DERIVATIVES, A PROCESS FOR THE PREPARATION THEREOF AND FORMULATIONS CONTAINING THEM

This application is a 371 application of PCT/EP96/01919, filed May 08, 1996.

TECHNICAL FIELD

The present invention relates to 10-deacetyl-14β-hydroxybaccatine III of formula 1:

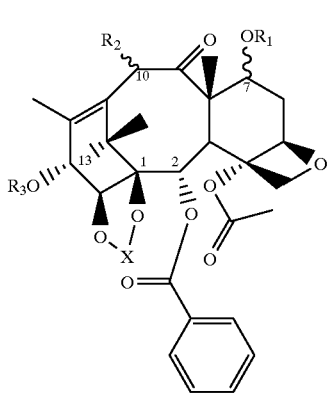

(1)

wherein

X is a >C=S, >C=NH or >S=O group;

$OR_1$, which can be α or β oriented, is a hydroxy, alkylsilyloxy (preferably triethylsilyloxy, O-TES), dichloromethoxycarbonyl group, $R_2$ is an α or β oriented hydroxy group, or a Troc group, or, with the carbon atom to which is connected, it forms a keto group;

$R_3$ is a isoserine residue of formula 2:

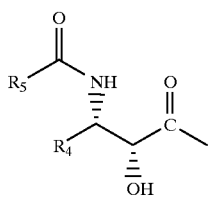

(2)

$R_4$ is a straight or branched alkyl or alkenyl group, having 1–5 carbon atoms, or an aryl group;

$R_5$ is an alkyl or alkenyl group, having 1–5 carbon atoms, or an aryl group, or a tert-butoxy group.

BACKGROUND ART

Paclitaxel (taxol), as it is already well-known, is a diterpenoid extracted from plants of the Taxus genus having anticancerogenic activity on different forms of human tumours. Its clinical use still involves some drawbacks such as cardiotoxicity and a poor water solubility, which makes its administration complex. Moreover, paclitaxel induces resistance quickly. Due to these reasons, researches have been in progress for some years aiming at synthesizing novel paclitaxel analogues which cause less adverse effects compared with the parent molecule.

SUMMARY OF THE INVENTION

Now it has been found that the compounds having the above reported formula 1, in addition to having a remarkable cytotoxic and antitumour activity, are free from the drawbacks of paclitaxel mentioned above.

According to the invention, the compounds of formula 1 are obtained by semisynthesis, starting from 10-deacetyl-14β-hydroxybaccatine. III which, upon protection of the hydroxyls at 7- and 10-, is reacted a) with thiophosgene in pyridine, thereby obtaining the corresponding 1,14-thiocarbonate, (1, with X=>C=S) or b) with thionyl chloride in the presence of tertiary bases (in which case a 1,14-sulfite will be obtained), (1, with X=>S=O) or c) with cyanogen bromide (after conversion of the hydroxyls at 1- and 14- into the corresponding lithium alkoxides), in order to obtain the iminocarbonate (1, with X=>C=NH). The operative details will be reported in the examples, and of course those skilled in the art will make use of well known variations when carrying out the process, without however departing from the original inventive scope.

DETAILED DESCRIPTION OF THE INVENTION

The resulting thiocarbonates, sulfites and iminocarbonates are esterified at the hydroxyl at $C_{13}$ with the suitably activated isoserine chains of formula 2, according to what reported in literature for the semisynthesis of paclitaxel and analogues thereof (see, for ex. EP-A 400,971; Fr. Dem. 86, 10400; E. Didier et. al. *Tetrahedron Letters* 35, 2349 (1994); E. Didier et al. *ibid.* 35, 3063 (1994)). Preferably the isoserine chains are used in the oxazolinedicarboxylic acid activated form corresponding to the formula 3:

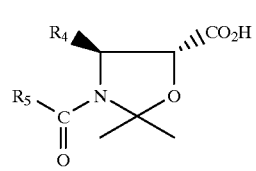

(3)

wherein $R_4$ and $R_5$ have the meanings defined above.

Alternatively to this synton, the analogous compound wherein the ketalizing acetone can be replaced by 1,3-bromoacetone, hexachloroacetone, chloral or an aromatic aldehyde, preferably p-methoxy benzaldehyde or o,p-dimethoxy benzaldehyde, can be used. The esterification of the oxazolidinecarboxylic acids with the taxane syntons and the subsequent elimination of the protecting groups are carried out as described in literature for the synthesis of paclitaxel and the analogues thereof.

The compounds of formula 1 wherein $R_2$ forms a keto group with $C_{10}$ can be obtained analogously, starting from 14β-hydroxy-10-dehydrobaccatine III.

Among the compounds of formula 1, particularly active proved to be 13-[(2R,3S)-3-tert-butoxycarbonyl-amino-2-hydroxy-3-isobutyl-propanoyl]-14β-hydroxybaccatine III 1,14-thiocarbonate (5), 13-[(2R,3S)-3-tert-butoxycarbonylamino-2-hydroxy-3-isobutenyl-propanoyl]-14β-hydroxybaccatine III 1,14-thiocarbonate (6), 13-[(2R,3S)-3-caproylamino-2-hydroxy-3-isobutenyl-propanoyl]-14β-hydroxybaccatine III 1,14-thiocarbonate III (7); active and with a different solubility in water proved to be the analogous derivatives having as substituents at the 1,14 hydroxyls the >C=NH group or the >S=O group. The compounds 13-[(2R,3S)-3-caproylamino-2-hydroxy-3- isobutenyl-propanoyl]-14β-hydroxybaccatine III 1,14-iminocarbonate (8) and 13-[(2R,3S)-3-caproylamino-2-hydroxy-3-isobutenyl-propanoyl]-14β-hydroxybaccatine-III 1,14-sulfite (9) showed advantages compared with the compounds of the prior art in terms of both activity and tolerability.

EXAMPLES

The cytotoxicity data of the compounds 5, 8 and 9 compared with those of paclitaxel are reported in the following Table, by way of example.

TABLE $IC_{50}$ of the compounds 5, 8 and of paclitaxel on six tumour cell lines.

| Cell line | Exposure time (h) | Paclitaxel | $IC_{50}$ (nm) 5 | 8 | 9 |
|---|---|---|---|---|---|
| L1210 (murine leukemia) | 72 | 7.5 ± 2.0 | 0.5 ± 0.1 | 2.4 ± 0.1 | 1.8 ± 0.1 |
| A121 (Human ovarian) | 72 | 4.7 ± 0.3 | 0.8 ± 0.3 | 1.9 ± 0.2 | 1.1 ± 0.1 |
| A549 (Human NSCLC) | 72 | 5.7 ± 0.5 | 2.3 ± 0.3 | 2.1 ± 0.3 | 1.8 ± 0.2 |
| HT-29 (Human colon) | 72 | 6.9 ± 0.4 | 0.3 ± 0.1 | 0.5 ± 0.1 | 0.5 ± 0.1 |
| MCF7 (Human breast) | 72 | 4.8 ± 0.1 | 1.2 ± 0.2 | 0.8 ± 0.2 | 1.0 ± 0.3 |
| MCF7-ADR (resistant) | 72 | 395 ± 8.7 | 18 ± 2.2 | 21 ± 6.2 | 16 ± 4.9 |

Standard conditions: basal medium=RPMI 1640+20 mM HEPES+2 mM L-glutamine.

The compounds of formula 1 show surprising advantages compared with paclitaxel on cell lines resistant to other anti-tumour substances, such as adriamycin or cis-platinum. The differences between paclitaxel and these products are even more evident in in vivo models, such as the athymic nude mouse with human tumour implant. The products of the invention can be incorporated in suitable pharmaceutical formulations for the administration of the products both parenterally and orally. For the intravenous administration, mixtures of Chremoform L and ethanol, polysorbates or liposomial preparations prepared with natural or synthetic phosphatidylcholine, or mixtures of natural phospholipids in the presence of cholesterol, are mainly used, furthermore formulations with micronized compounds with particle size below 300 nm are used. The compounds are administered to the man at concentrations ranging from 30 to 500 mg/m$^2$.

The examples reported below further illustrated the invention.

Example 1—Preparation of 7,10-DiTroc-14β-hydroxy-10-deacetylbaccatine III 1,14-iminocarbonate.

A solution of 205 mg of 7,10-DiTroc-14β-hydroxy-10-deacetyl baccatine III (prepared according to U.S. Pat. No. 5,254,591) in 5 ml of tetrahydrofuran is added with 336 μl of a 1.6 M solution of butyl-lithium in n-hexane at 0° C., followed by the addition 45.6 mg of cyanogen bromide. After stirring for 10 minutes at 0° C. the reaction mixture is left under stirring at room temperature for 20 minutes, during which time the reaction products disappear; the reaction mixture is treated with a NaHCO$_3$ saturated solution in the presence of methylene chloride. The organic phase is washed with cold water and concentrated after drying over Na$_2$SO$_4$. The residue is purified through a silica gel column, eluting the desired compound with a chloroform/acetone 3:1 mixture. 140 mg of iminocarbonate are obtained.

Example 2—Preparation of 7,10-DiTroc-14β-hydroxy-10-deacetylbaccatine III 1,14-sulfite.

A solution of 100 mg of 7,10-DiTroc-14β-hydroxydeacetylbaccatine III in 1.5 ml of methylene chloride is added with 63 μl (46 mg) of triethylamine and subsequently 12 μl (19.6 mg) of SOCl$_2$ diluted in 200 μl of methylene chloride; the reaction mixture is stirred at 0° C. for 10 minutes, then is diluted with 10 vol. of methylene chloride and shaken with water in the presence of ice, washing thoroughly to neutrality. The organic phase is concentrated to dryness and the residue is chromatographed on silica gel, eluting the reaction product with an hexane/ethyl acetate 1:1 mixture. 74 mg of cyclic sulfite are obtained, which is a mixture of diastereomers at the sulfur atom.

Example 3—Preparation of 7-O-Tes-14β-hydroxybaccatine III 1,14-sulfite.

A solution of 100 mg of 7-O-Tes-14β-hydroxy-10-deacetylbaccatine III (U.S. Pat. No. 5,264,591) in 1.5 ml of methylene chloride is added with 63 μl (46 mg) of triethylamine and subsequently 12 μl (19.6 mg) of SOCl$_2$ diluted in 200 μl of methylene chloride; the reaction mixture is stirred at 0° C. for 10 minutes, then is diluted with 10 vol. of methylene chloride and shaken with water in the presence of ice, washing thoroughly to neutrality.

The organic phase is concentrated to dryness and the residue is chromatographed on silica gel, eluting the reaction product with a methylene chloride/methanol 95:5 mixture. 81 mg of 7-O-Tes-14β-hydroxy-10-deacetylbaccatine III cyclic sulfite are obtained, which is a mixture of diastereomers at the sulfur atom.

50 mg of reaction product are dissolved in 1 ml of anhydrous pyridine and added with 30 μl of acetyl chloride at 0° C. under strong stirring. After 5 h at 0° C. the reaction mixture is poured into 10 ml of water and is immediately extracted for three times with 10 ml each of ethyl acetate. The organic phase is washed with diluted HCl to remove pyridine and finally with a NaCl saturated solution to neutrality; the organic phase is dried and concentrated to dryness. 46 mg of 14-β-hydroxy-baccatine III 7-O-Tes-1,14-sulfite are obtained.

Example 4—Preparation of 14β-hydroxy-10-deacetyl-baccatine III 7-O-Tes-1,14-thiocarbonate.

a) A suspension of 2.8 g of 14β-hydroxy-10-deacetylbaccatine III in 25 ml of methylene chloride is added with 8.3 ml of anhydrous pyridine; the resulting solution is cooled at −15° C. and is added dropwise with 26.6 ml of a 1.9 M thiophosgene solution, under nitrogen atmosphere and with stirring, during 10 minutes. A precipitate forms; the reaction mixture, after checking by TLC (hexane/ethyl acetate 7:3), is treated with a NaHCO$_3$ solution to completely destroy phosgene. After dilution with water, the mixture is extracted with methylene chloride. The yellowish organic phase is washed with diluted HCl and then with water to neutrality. The organic phase, after drying over $Na_2SO_4$, is concentrated to dryness. 2.7 g of 14β-hydroxy-10-deacetyl-baccatine III 1,14-thiocarbonate are obtained.

b) 500 mg of 14β-hydroxy-10-deacetylbaccatine III 1,14-thiocarbonate are dissolved in 5 ml of DMF and treated with 287 μl of Tes-chloride and 116 mg of imidazole, adding the silylating agent dropwise under stirring. After 2 h, the reaction mixture is added with celite and poured onto ice. The precipitate, after thorough washing with water, is washed with hexane to remove the silanol and then is extracted with methylene chloride. By concentration of the organic phase, 14β-hydroxy-10-deacetylbaccatine III 7-O-Tes-1,14-thiocarbonate is obtained, having a sufficient purity for the subsequent reactions. Alternatively, the residue is chromatographed over 10 g of silica gel, eluting with an hexane/ethyl acetate 1:1 mixture. 490 mg of product are obtained, $M^+$a m/z 602.

Example 5—Preparation of 14β-hydroxybaccatine III 7-O-Tes-1,14-thiocarbonate, 500 mg of 14β-hydroxy-10-deacetyl-baccatine III 7-O-Tes-1,14-thiocarbonate are dissolved in 10 ml of anhydrous pyridine and added with 200 μl of acetyl chloride at 0° C. under strong stirring. After 5 h at 0° C., the reaction mixture is poured into 100 ml of water and is immediately extracted for three times with 50 ml each of ethyl acetate. The organic phase is washed with diluted HCl to remove pyridine and finally with a NaCl saturated solution to neutrality; the organic phase is dried and concentrated to dryness. 501 mg of 14β-hydroxybaccatine III 7-O-Tes-1,14-thiocarbonate are obtained.

Example 6—Preparation of 13-[(2R.3S)-3-terbutoxy-carbonyl-amino-2-hydroxy-3-isobutyl-propanoyl]-14β-hydroxybaccatine III 1,14-thiocarbonate.

0.5 g of 7-O-triethylsilyl-14β-hydroxybaccatine III 1,14-thiocarbonate are dissolved in 60 ml of toluene. The solution is added with 800 mg of (4S,5R)-N-(tert-butoxycarbonyl)-2,2-dimethyl-4-isobutyl-5-oxazolidine-carboxylic acid, 400 mg of cyclohexylcarbodiimide and 40 mg of N,N-dimethylaminopyridine. The reaction mixture is kept at 80° C. for two hours, then is filtered and washed with water; the organic phase is then concentrated to dryness. The residue is treated with methanol containing 0.1% of $H_2SO_4$, at 10° C. The methanol solution is diluted with water and the product is extracted with ethyl acetate; the organic phase is concentrated to dryness and the residue is chromatographed on silica gel, eluting with acetone/hexane 4:6. Are obtained 580 mg of 5, $M^+$a m/z 887.

Example 7—Preparation of 13-[(2R.3S)-3-tert-butoxycarbonyl-amino-2-hydroxy-3-isobutyl-propanoyl]-14β-hydroxybaccatine III 1,14-iminocarbonate.

0.7 g of 7,10-of-Troc-14β-hydroxybaccatine III 1,14-iminocarbonate are dissolved in 80 ml of toluene. The solution is added with 750 mg of (4S,5R)-N-(tert-butoxycarbonyl)-2,2-dimethyl-4-isobutyl-5-oxazolidine-carboxylic acid, 400 mg of cyclohexylcarbodiimide and 40 mg of N,N-dimethylaminopyridine. The reaction mixture is kept at 80° C. for two hours. The reaction mixture is filtered and washed with water and the organic phase is then concentrated to dryness. The residue is treated with methanol containing 0.1% of $H_2SO_4$ at 10° C.; after partial dilution with water and further acidification with acetic acid, the solution is treated with Zn to remove Troc. The hydromethanol solution is diluted with water and the product is extracted with ethyl acetate; the organic phase is concentrated to dryness and the residue is chromatographed on silica gel, eluting with acetone/hexane 4:6. 480 mg of product are obtained, $M^+$a m/z 841.

Example 8—Preparation of 13-[(2R.3S)-3-caproyl-amino-2-hydroxy-3-isobutyl-propanoyl]-14β-hydroxybaccatine III 1,14-thiocarbonate.

0.5 g of 7-O-triethylsilyl-14β-hydroxybaccatine III 1,14-thiocarbonate are dissolved in 60 ml of toluene. The solution is added with 750 mg of (4S,5R)-N-(caproyl)-2,2-dimethyl-4-isobutyl-5-oxazolidine-carboxylic acid, 400 mg of cyclohexylcarbodiimide and 40 mg of N,N-dimethylaminopyridine. The reaction mixture is kept at 80° C. for two hours, filtered and washed with water, and the organic phase is then concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 4:6. 502 mg of desired product are obtained.

Example 9—Preparation of 13-[(2R.3S)-3-caproyl-amino-2-hydroxy-3-isobutyl-propanoyl]-14β-hydroxybaccatine III 1,14-sulfite.

0.5 g of 7-O-triethylsilyl-14β-hydroxybaccatine III 1,14-sulfite are dissolved in 60 ml of toluene. The solution is added with 750 mg of (4S,5R)-N-(caproyl)-2,2-dimethyl-4-isobutyl-5-oxazolidine-carboxylic acid, 400 mg of cyclohexylcarbodiimide and 40 mg of N,N-dimethylaminopyridine. The reaction mixture is kept at 80° C. for two hours, filtered and washed with water, and the organic phase is then concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 4:6. 502 mg of desired product are obtained.

Example 10—Preparation of 13-[(2R.3S)-3-caproyl-amino-2-hydroxy-3-isobutenyl-propanoyl]-14β-hydroxybaccatine III 1,14-thiocarbonate.

0.5 g of 7-O-triethylsilyl-14β-hydroxybaccatine III 1,14-thiocarbonate are dissolved in 60 ml of toluene. The solution is added with 750 mg of (4S,5R)-N-(caproyl)-2,2-dimethyl-4-isobutenyl-5-oxazolidine-carboxylic acid, 400 mg of cyclohexylcarbodiimide and 40 mg of N,N-dimethylaminopyridine. The reaction mixture is kept at 80° C. for two hours. The reaction mixture is filtered and washed with water and the organic phase is then concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 3:7. 445 mg of desired product are obtained.

Example 11—Preparation of 13-[(2R.3S)-3-caproyl-amino-2-hydroxy-3-isobutenyl-propanoyl]-14β-hydroxybaccatine III 1,14-sulfite.

0.5 g of 7-O-triethylsilyl-14β-hydroxybaccatine III 1,14-sulfite are dissolved in 60 ml of toluene. The solution is added with 750 mg of (4S,5R)-N-(caproyl)-2,2-dimethyl-4-isobutenyl-5-oxazolidine-carboxylic acid, 400 mg of cyclohexylcarbodiimide and 40 mg of N,N-dimethylaminopyridine. The reaction mixture is kept at 80° C. for two hours. The reaction mixture is filtered and washed with water and the organic phase is then concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 7:3. 495 mg of desired product are obtained.

Example 12—Preparation of 13-[(2R,3S)-3-caproyl-amino-2-hydroxy-3-crotonyl-propanoyl]-14β-hydroxybaccatine III 1,14-thiocarbonate.

0.5 g of 7-O-triethylsilyl-14β-hydroxybaccatine III 1,14-thiocarbonate are dissolved in 60 ml of toluene. The solution is added with 760 mg of (4S,5R)-N-(caproyl)-2,2-dimethyl-4-crotonyl-5-oxazolidine-carboxylic acid, 400 mg of cyclohexylcarbodiimide and 40 mg of N,N-dimethylaminopyridine. The reaction mixture is kept at 80° C. for two hours. The reaction mixture is filtered and washed with water and the organic phase is then concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 2:8. 430 mg of desired product are obtained.

Example 13—Preparation of 7-O-Tes-10-dehydro-14β-hydroxybaccatine III 1,14-thiocarbonate a) 14β-Hydroxy-10-dehydrobaccatine III 10 g of 10-deacetyl-14β-hydroxybaccatine III are suspended in 350 ml of methanol and added with 65 g of $Cu(OAc)_2$. The suspension is stirred at room temperature for 120 h. The salts are filtered off, the solution is evaporated to dryness and the residue is chromatographed on 100 g of silica gel, eluting with an hexane/ethyl acetate 6:4 mixture. After crystallization from ligroin, 9.3 g of 6 are obtained, $M^+$a m/z 558.

b) Title compound 0.5 g of 14β-hydroxy-10-dehydrobaccatine are treated according to the procedure of Example 4 a). 350 mg of the desired product are obtained.

Example 14—Preparation of 13-[(2R.3S)-3-caproyl-amino-2-hydroxy-3-crotonyl-propanoyl]10-dehydro-14β-hydroxy-baccatine III 1,14-thiocarbonate.

0.5 g of 7-O-triethylsilyl-10-dehydro-14β-hydroxy-baccatine III 1,14-thiocarbonate are dissolved in 60 ml of toluene. The solution is added with 760 mg of (4S,5R)-N-(caproyl)-2,2-dimethyl-4-crotonyl-5-oxazolidine-carboxylic acid, 400 mg of cyclohexylcarbodiimide and 40 mg of N,N-dimethylaminopyridine. The reaction mixture is kept at 80° C. for two hours. The reaction mixture is filtered and washed with water and the organic phase is then concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 2:8. 430 mg of desired product are obtained.

What is claimed is:
1. Compounds of formula 1:

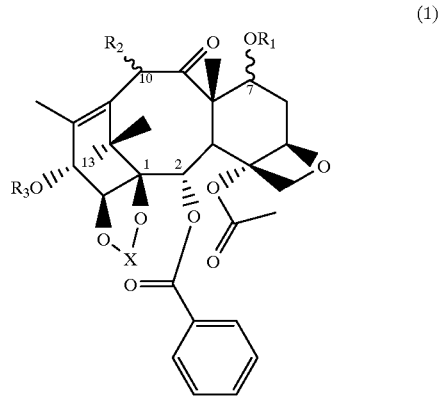

(1)

wherein

X is a >C=S, >C=NH or >S=O group;

$OR_1$, which can be α or β oriented, is a hydroxy, alkylsilyloxy dichloromethoxycarbonyl group, $R_2$ is an α or β oriented hydroxy group, or a Troc group, or, with the carbon atom to which is connected, it forms a keto group;

$R_3$ is a isoserine residue of formula 2:

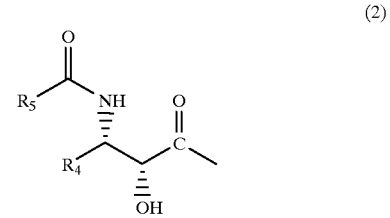

(2)

$R_4$ is a straight or branched alkyl or alkenyl group, having 1–5 carbon atoms, or an aryl group;

$R_5$ is an alkyl or alkenyl group, having 1–5 carbon atoms, or an aryl group, or a tert-butoxy group.

2. A compound of formula 1, selected from the group consisting of:

7,10-DiTroc-14β-hydroxy-10-deacetylbaccatine III 1,14-iminocarbonate;

7,10-DiTroc-14β-hydroxy-10-deacetylbaccatine III 1,14-sulfite;

7-O-Tes-14p-hydroxybaccatine III 1,14-sulfite;

14β-hydroxy-10-deacetylbaccatine III 7-O-Tes-1,14-thiocarbonate;

14β-hydroxybaccatine III 7-O-Tes-1,14-thiocarbonate;

13-[(2R,3S)-3-tert-butoxy-carbonyl-amino-2-hydroxy-3-isobutylpropanoyl]-14p-hydroxybaccatine III 1,14-thiocarbonate;

13-[(2R,3S)-3-tert-butoxy-carbonyl-amino-2-hydroxy-3-isobutylpropanoyl]-14β-hydroxybaccatine III 1,14-iminocarbonate;

13-[(2R,3S)-3-caproyl-amino-2-hydroxy-3-isobutylpropanoyl]-14β-hydroxybaccatine III 1,14-thiocarbonate;

13-[(2R,3S)-3-caproyl-amino-2-hydroxy-3-isobutylpropanoyl]-14β-hydroxybaccatine III 1,14-sulfite;

13-[(2R,3S)-3-caproyl-amino-2-hydroxy-3-isobutenylpropanoyl]-14β-hydroxybaccatine III 1,14-thiocarbonate;

13-[(2R,3S)-3-caproyl-amino-2-hydroxy-3-isobutenylpropanoyl]-14p-hydroxybaccatine III 1,14-sulfite;

13-[(2R,3S)-3-caproyl-amino-2-hydroxy-3-crotonyl-propanoyl]-14β-hydroxybaccatine III 1,14-thiocarbonate;

7-O-Tes-10-dehydro-14β-hydroxybaccatine III 1,14-thiocarbonate;

13-[(2R,3S)-3-caproyl-amino-2-hydroxy-3-crotonyl-propanoyl]10-dehydro-14p-hydroxybaccatine III 1,14-thiocarbonate;

13-[(2R,3S)-3-tert-butoxycarbonylamino-2-hydroxy-3-isobutenylpropanoyl]-14p-hydroxybaccatine III 1,14-thiocarbonate; and 13-[(2R,3S)-3-caproylamino-2-hydroxy-3-isobutenylpropanoyl]-14β-hydroxybaccatine III 1,14-iminocarbonate.

3. A process for the preparation of the compounds of formula 1, which process comprises the following steps:

i) reacting 10-deacetyl-14β-hydroxybaccatine III [(respectively 10-dehydro-14,β-hydroxybaccatine III)], upon protection of the hydroxyls at 7- and 10-positions [(respectively of the hydroxyl at 7-)]:

a) with thiophosgene in pyridine, to form the corresponding 1,14-thiocarbonate, or b) with thionyl chloride in the presence of a tertiary base to form the corresponding 1,14-sulfite, or c) with butyl lithium and cyanogen bromide, to form the corresponding 1,14-iminocarbonate to form intermediates;

ii) esterifying the resulting intermediates at position 13 with an activated isoserine; and iii) finally deprotecting the hydroxy groups to obtain the compounds.

4. A process according to claim 3, in which process the esterification at position 13 is carried out with activated isoserines of formula 3:

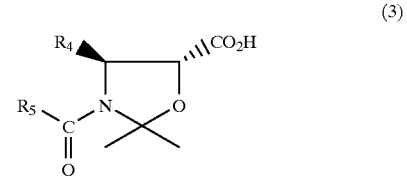

(3)

wherein $R_4$ and $R_5$ have the meanings defined above or with corresponding ketals with 1,3-bromoacetone, hexachloroacetone, chloral, p-methoxy- or o,p-dimethoxy benzaldehyde.

5. Pharmaceutical compositions with antitumour activity, having a reduced cardiotoxicity, containing one or more compounds of formula 1.

* * * * *

UNITED STATES PATENT AND TRADEMARK OFFICE
CERTIFICATE OF CORRECTION

PATENT NO. : 5,917,056
DATED : June 29, 1999
INVENTOR(S) : E. Bombardelli

It is certified that error appears in the above-identified patent and that said Letters Patent is hereby corrected as shown below:

Title page, item [54] and col. 1, line 1, change "HYDROXYBACCACTINE" to --HYDROXYBACCATINE--.

Column 8, line 24: after "silyloxy" insert --,--.

Column 8, line 25: after "group" and before "," insert --(Troc=Cl$_3$CCH$_2$COO-)--.

Column 8, line 51: change "14p" to --14β--.

Column 8, line 56: change "14p" to --14β--.

Column 9, line 5: change "14p" to --14β--.

Column 9, line 13: change "14p" to --14β--.

Column 9, line 17: change "14p" to --14β--.

Column 9, line 25: delete "[(respectively 10 dehydro-14,β-hydroxybaccatine".

Column 9, line 26: delete "III)]".

Column 9, line 27: delete "[(respectively of the hydroxyl at 7-)]".

Signed and Sealed this

Eleventh Day of January, 2000

Attest:

Q. TODD DICKINSON

*Attesting Officer*   Acting Commissioner of Patents and Trademarks